United States Patent
Strumor

[11] Patent Number: 6,135,286
[45] Date of Patent: Oct. 24, 2000

[54] THERMALLY INSULATING EMERGENCY CONTAINERS WITH O-RING CONSTRUCTION

[76] Inventor: Mathew A Strumor, 158 Key Heights Dr., Tavernier, Fla. 33070

[21] Appl. No.: 09/413,002

[22] Filed: Oct. 5, 1999

Related U.S. Application Data

[63] Continuation-in-part of application No. 09/174,674, Oct. 19, 1998, which is a continuation-in-part of application No. 08/854,257, May 9, 1997, abandoned.

[51] Int. Cl.[7] .................................................. B65D 69/00
[52] U.S. Cl. ......................... 206/573; 206/803; 215/228; 220/23.8; 220/212; 220/304
[58] Field of Search .................................. 206/543, 545, 206/570, 528, 540, 573, 803, 459.1, 541, 581; 220/304, 288, 592.05, 23.83, 23.8, 212, 377; 215/228, 230

[56] References Cited

U.S. PATENT DOCUMENTS

| | | | |
|---|---|---|---|
| 4,225,052 | 9/1980 | Tector et al. | 220/23.8 |
| 4,444,324 | 4/1984 | Grenell | 206/545 |
| 4,515,272 | 5/1985 | Newhouse | 206/591 |
| 4,573,581 | 3/1986 | Galloway et al. | 206/570 |
| 4,586,456 | 5/1986 | Forward | 206/803 |
| 4,804,101 | 2/1989 | Heath | 220/23.83 |
| 4,807,776 | 2/1989 | Cortopassi | 220/23.83 |
| 5,765,683 | 6/1998 | Starkle | 206/803 |
| 5,787,839 | 8/1998 | Magnant et al. | 206/545 |

FOREIGN PATENT DOCUMENTS 649541 1/1951 United Kingdom .................. 220/23.8

*Primary Examiner*—Paul T. Sewell
*Assistant Examiner*—Luan K. Bui
*Attorney, Agent, or Firm*—Richard L. Huff

[57] ABSTRACT

A thermally insulating luminous container with an O-ring construction having a primary container having inner and outer walls and a removable cover. A plurality of secondary containers may be affixed to the outer wall of the primary container, which secondary containers have inner and outer walls and removable attached covers. The container may be constructed by blow-molding hypoallergenic thermoplastic material, and may contain a compass and a signaling mirror. These containers are suitable for holding water, oxygen supplements and enhancers, food, medicines and first aid supplies. The containers may be supplied to survivors of natural disasters or used for general utility.

18 Claims, 6 Drawing Sheets

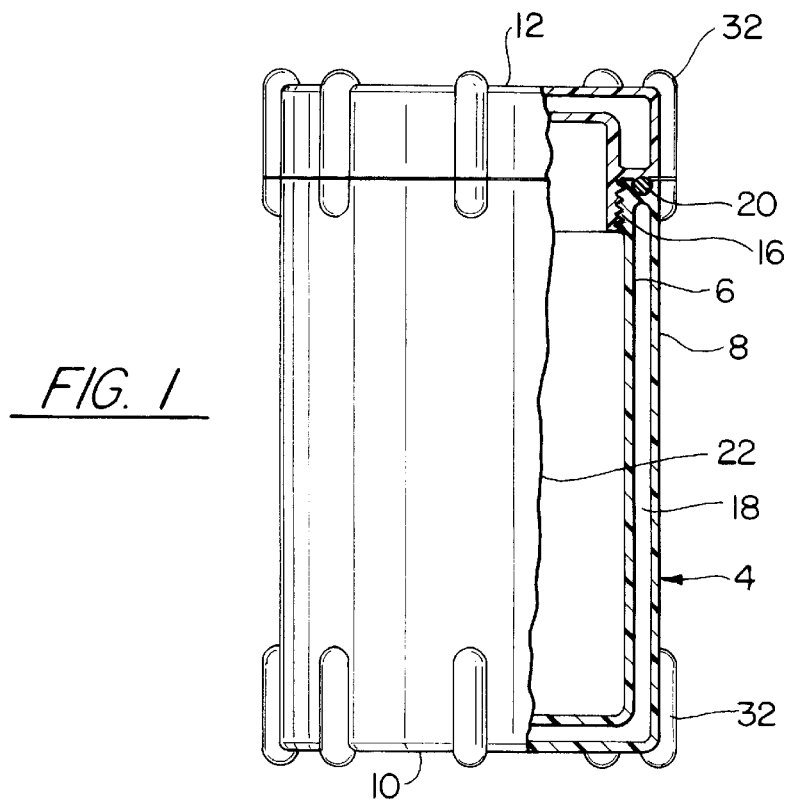
FIG. 1
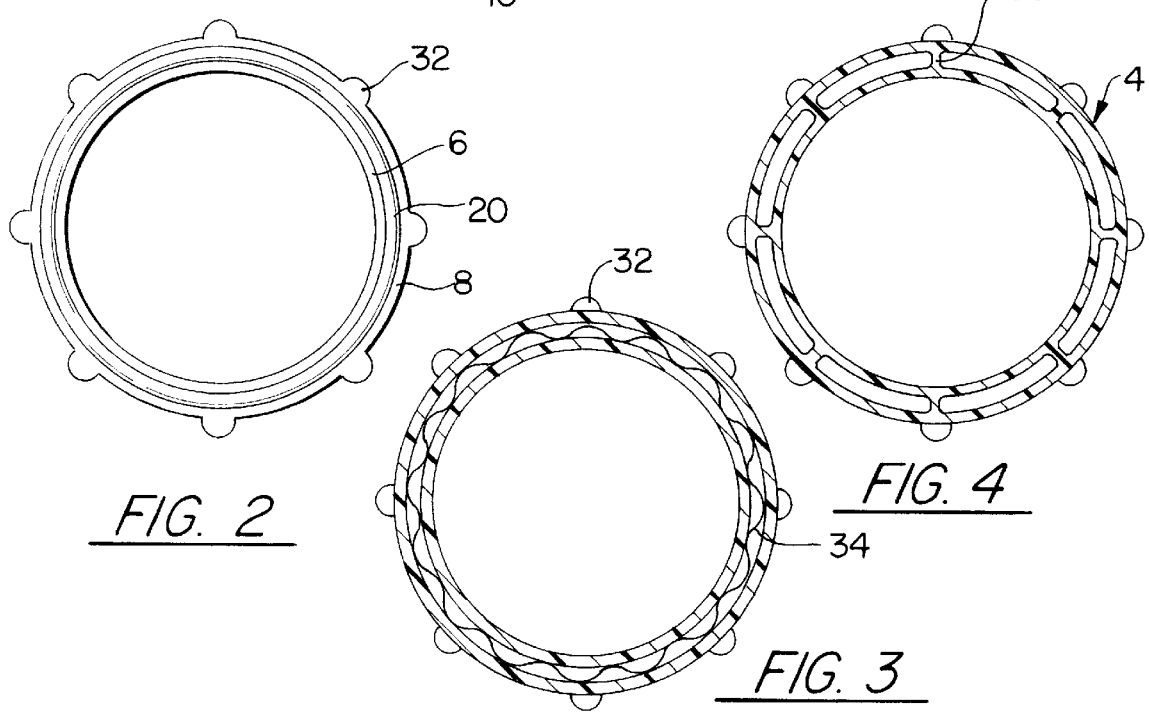
FIG. 2
FIG. 3
FIG. 4

THERMALLY INSULATING EMERGENCY CONTAINERS WITH O-RING CONSTRUCTION

REFERENCE TO RELATED APPLICATIONS

This application is a continuation-in-part of my co-pending application, Ser. No. 09/174,674, filed Oct. 19, 1998 which is a continuation-in-part of my application, Ser. No. 08/854,257, filed May 9, 1997, now abandoned.

BACKGROUND OF THE INVENTION

1. Field of the Invention

The field of this invention is thermally insulating containers with an O-ring construction for everyday use and for emergency containers for disasters. The containers of this invention protect their ingredients from temperature changes and are useful for distributing pills, tablets and mini-bars, water, dehydrated food, vitamins, supplements, a first aid kit, and necessary supplies in times of disasters.

2. Description of the Related Art

The art is aware of thermal storage containers for food. U.S. Pat. No. 4,444,324 to Grenell shows compartmentalized thermally insulating containers for food, etc. These compartmentalized containers are made so that each compartment is the same size. These containers would be difficult to find at night if their use as emergency containers was attempted, and these containers would offer no help in signaling for help or in directionally orienting the user. These containers do not have O-rings between the covers and the container to protect against leakage and temperature changes. These containers do not have covers that are attached by a connection. Therefore the covers of the prior art containers can become lost.

SUMMARY OF THE INVENTION

One object of the present invention is to overcome the deficiencies of the prior art containers. This object is accomplished by providing containers for pills, tablets, mini-bars, water, and other necessary items, which containers are thermally insulated, compartmentalized, sturdy, and provide features which are helpful in times of disaster. It is an object of the present invention to provide the above containers while avoiding the inadequacies inherent in the products of the prior art.

Another object of the present invention is directed to thermally insulating containers having an inside and an outside wall and may have a single, primary container or may have a plurality of secondary containers affixed to the outer cylinder wall of the primary container. All of the containers are double walled to provide protection against changes in temperate and impact on delivery. The thermally insulating containers, which are made of hypo-allergenic material, have multiple purposes, and can serve as containers for healthful pills, tablets and mini-bars, water, first aid supplies, vitamins and supplements, dehydrated food, etc. The primary and secondary containers have openings at the top ends. For specialized utility during disaster relief, a container is luminous to provide for ease in locating, it contains a signaling mirror for summoning aid, and has a compass for assistance in getting oriented. At least one of the outer, secondary containers is part of a disaster container. These secondary containers can be removed for easy use and returned to the primary container and covered. The covers of the containers are attached so as not to become lost. The present invention provides secondary containers of varying sizes in order to provide thermally insulating containers for everyday use such as single thermally insulating containers for pills, tablets and mini-bars. At least one secondary container may serve as a squeezable thermally insulating tube for burn ointments, food products in paste form, sun protective creams, or insect repellents. Another secondary container may serve as a firm thermally insulating container for creams and salves. Another secondary container comprises an upper portion and a removable lower portion.

A primary function of the containers of this invention is to hold oxygen enhancers, water, food supplements, and supplies for disaster survivors until help arrives. Another function is to serve as carriers for these compact supplies in outer space operations or in other operations where these compact supplies are not readily available as back-up emergency supplies.

BRIEF DESCRIPTION OF THE DRAWING

FIG. 1 is an elevational side view, partly in section, of a primary container of one embodiment of the present invention.

FIG. 2 is a horizontal cross-sectional view of the primary or secondary container of the present invention showing the O-ring between the cover and the container wall.

FIG. 3 is a horizontal cross-sectional view of a primary or secondary container of one embodiment of the invention showing strengthening corrugation molded as part of the wall of the inside container.

FIG. 4 is a horizontal cross-sectional view of another embodiment of the primary or secondary container of the present invention showing strengthening units molded between the inside and outside walls.

DESCRIPTION OF THE PREFERRED EMBODIMENTS

Figure 5:
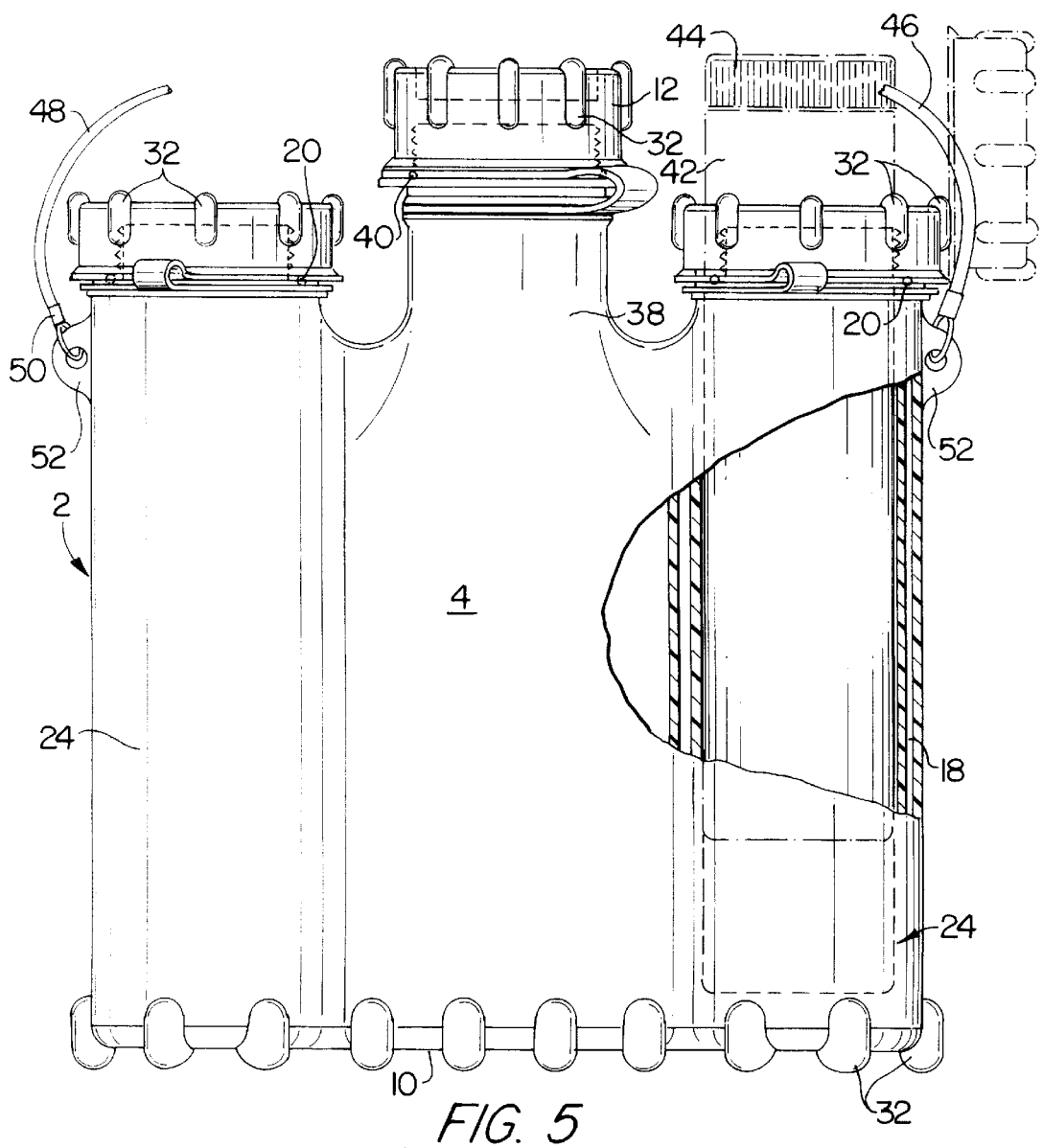
FIG. 5 is an elevational side view, partially in section, of the primary container showing the O-ring between the container and the container wall and showing the attachment of the covers to the container and the lanyard holders.
Figure 6:
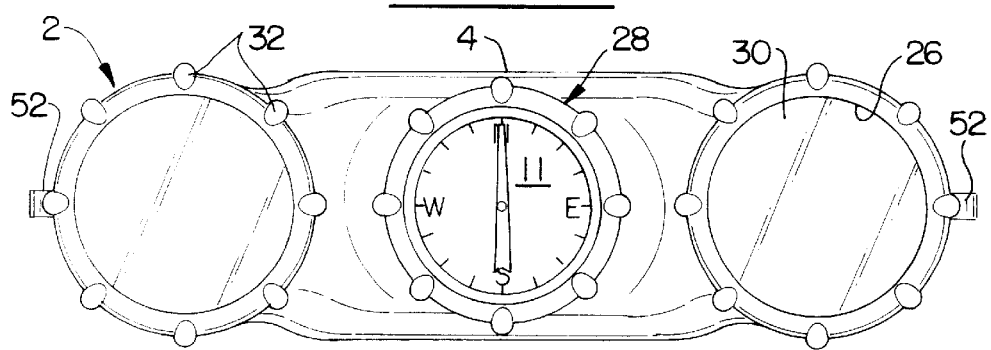
FIG. 6 is a top plan view of the primary container showing a compass in the cover attachment and the lanyard holders.

The present invention will now be described with reference to the above drawing, like numerals referring to like parts throughout the description.

Referring to FIGS. 1–11, the preferred emergency containers 2 are constructed of rugged plastic by the blow molding process.

A preferred container 2 according to the present invention contains a primary container 4 having inner 6 and outer 8 cylindrical walls, a bottom 10, and a removable screw cover 12 which is attached by a connecting strap 14 to a threaded opening 16 to prevent loss. The space 18 between the inner 6 and outer 8 walls forms a thermally insulating space 18. The primary container 4 has a cylindrical inner shape. The primary container 4 has an O-ring 20 between the container body 22 and the cover 12. The container 4 further contains a plurality of secondary containers 24 affixed to the outer cylindrical wall 8 of the primary container 4, which secondary containers 24 have removable screw-top covers 12 attached to the body portions 22 of the secondary containers 24, thermal insulating spaces 18, and O-rings 20 to ensure a tight seal.

It is preferred that the top central cover 12 is circular in shape and has an indentation 26 which contains a compass 28 in order to help disaster survivors regain their orientation. Also, it is preferred that the secondary container 24 or the primary container 4 has a metal signaling mirror 30 attached to a cover 12 thereof Such mirror 30 should be made of stainless steel rather than glass to avoid breakage.

Since relief efforts are carried out during the night as well as during the day, it is preferred that the containers 2 of the present invention be coated with luminous paint so as to be visible to disaster survivors. Optionally, the containers 2 may be manufactured from plastic which has luminous materials incorporated therein.

The containers 2 contains sturdy bumpers 32 on both the top 12 and bottom 10 so as to protect the containers 2 during delivery. The bumpers 32 also serve as an ergonomic grip for helping in opening and closing the covers 12.

In order to form a tight seal for protection of the contents during storage and delivery, there is an O-ring 20 placed at the top of the inner 6 and outer 8 wall, which O-ring 20 is compressed by the screw cover 12 when the primary container 4 or a secondary container 24 is closed. It is preferred that both the primary container 4 and all of the secondary containers 24 be equipped with an O-ring 20 for assurance of a tight seal.

In addition to containing a thermally insulating space 18 which aids in protecting the contents of the primary 4 and secondary 24 containers against changes in temperature, the space 18 between the inner 6 and outer 8 wall of these containers 4 24 may contain a corrugated sheet 34 incorporated in the blow molding process which adds strength to prevent damage on delivery. As an alternative to a corrugated sheet 34, strength may be provided by a plurality of connecting I-beam pieces 36 which connect the inner walls 6 and the outer walls 8 of these containers 4 24.

In a preferred embodiment, there is a plurality, preferably two, of secondary containers 24 around the periphery of the primary container 4. Each of these secondary containers 24 may be made from the same high-impact plastic material as the primary container 4 by blow molding the complete container 2 as a single piece. Each of these secondary containers 24 has a top screw-on cover 12 which is connected to a neck 38 by a connecting strap 14 to avoid loss of the cover 12. Also, each secondary container 24 has an outer wall 8 which is contiguous with the outer wall 8 of the primary container 4.

In a preferred embodiment of the secondary container 24, there is an outer wall 8, a thermally insulating space 18, and an inner wall 6. The outer wall 8 is fixedly attached to a screw neck 38 containing a screw-on cover 12. The screw neck 38 has a diameter essentially the same as the diameter of the outer wall 8. The neck 38 and cover 12 are connected by a connecting strap 14 which contains a circular ring 40 at each end which is slidable about the neck 38 and cover 12.

The inner wall 6 of the secondary container 24 is not affixed to the outer wall 8 and constitutes an insertable container 42 which may be removed from the outer wall 8 of the secondary container 24. The insertable container 42 has a screw-on top 44 which may be easily connected to the distal end 46 of a lanyard 48. A clip-on attachment (not shown) is preferred. The proximal end 50 of the lanyard 48 is fixedly attached to the outer wall 8 of the secondary container 24 by a connecting ring 52. Thus, when the insertable container 42 is removed from the secondary container 24, the lanyard 48 may be secured to the top 44 of the insertable container 42, and the top 44 may be removed without fear of loss.

Figure 7:
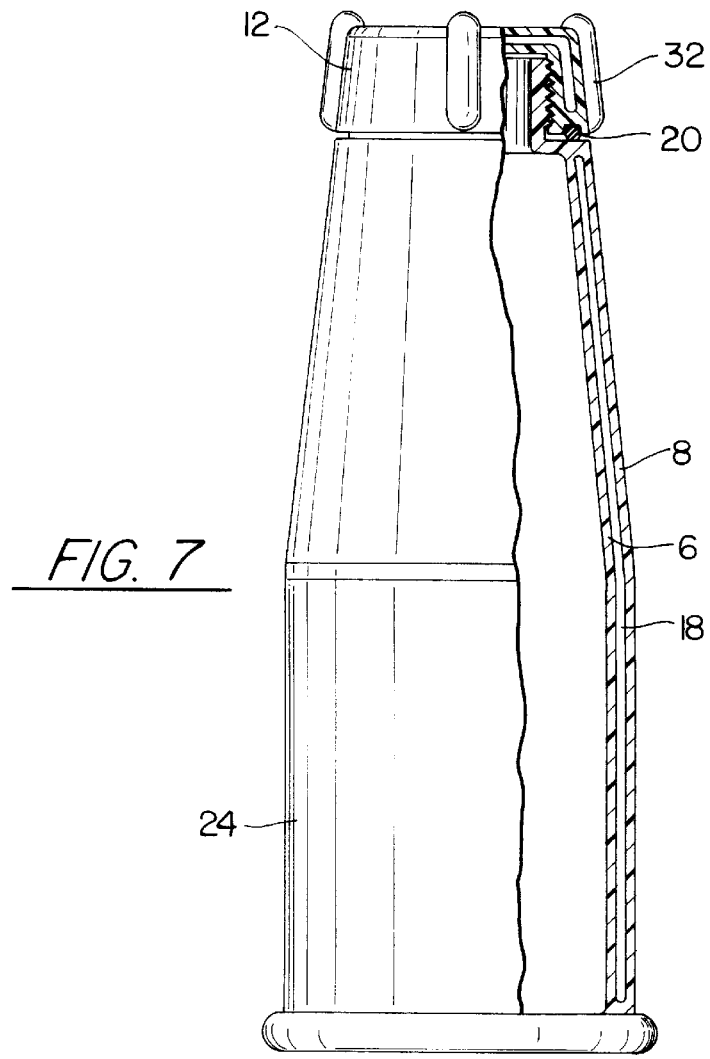
FIG. 7 is an elevational side view, partially in section, showing a thermally insulating squeezable container of this invention.

It is preferred that one of the secondary containers 24 has squeezable sides and thus is capable of holding liquids which may dispensed without waste in a zero-gravity environment or may dispense food or topical applications having a creamy consistency. One such ingredient is preferably sunscreen. Such secondary container is shown in FIG. 7.

Figure 8:
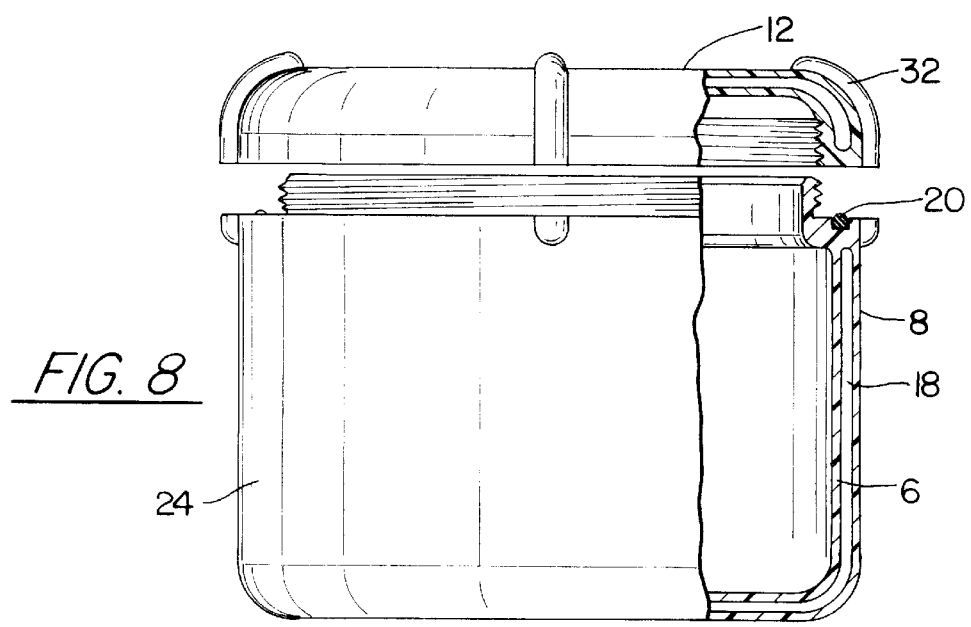
FIG. 8 is a side elevational view, partly in section, showing a thermally insulating cream container of this invention.

Another preferred secondary container 24 is an insulated container 24 having a screw top 44 and adapted to hold a topical application of cream consistency, such as sunscreen and face creams as shown in FIG. 8.

Figure 9:
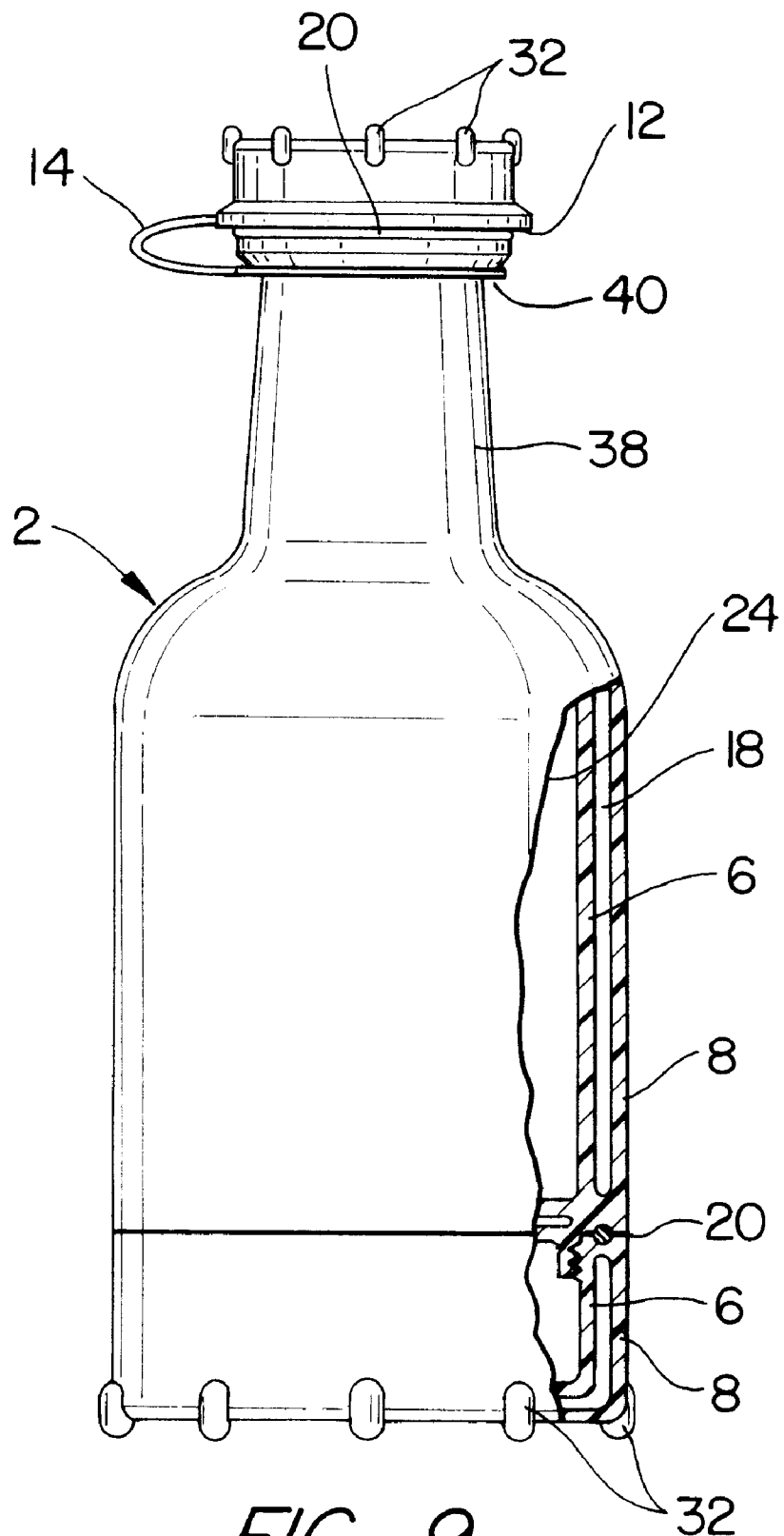
FIG. 9 is an elevational perspective view, partially cut away, of a thermally insulating secondary container having an upper compartment and a removable lower compartment.
Figure 10:
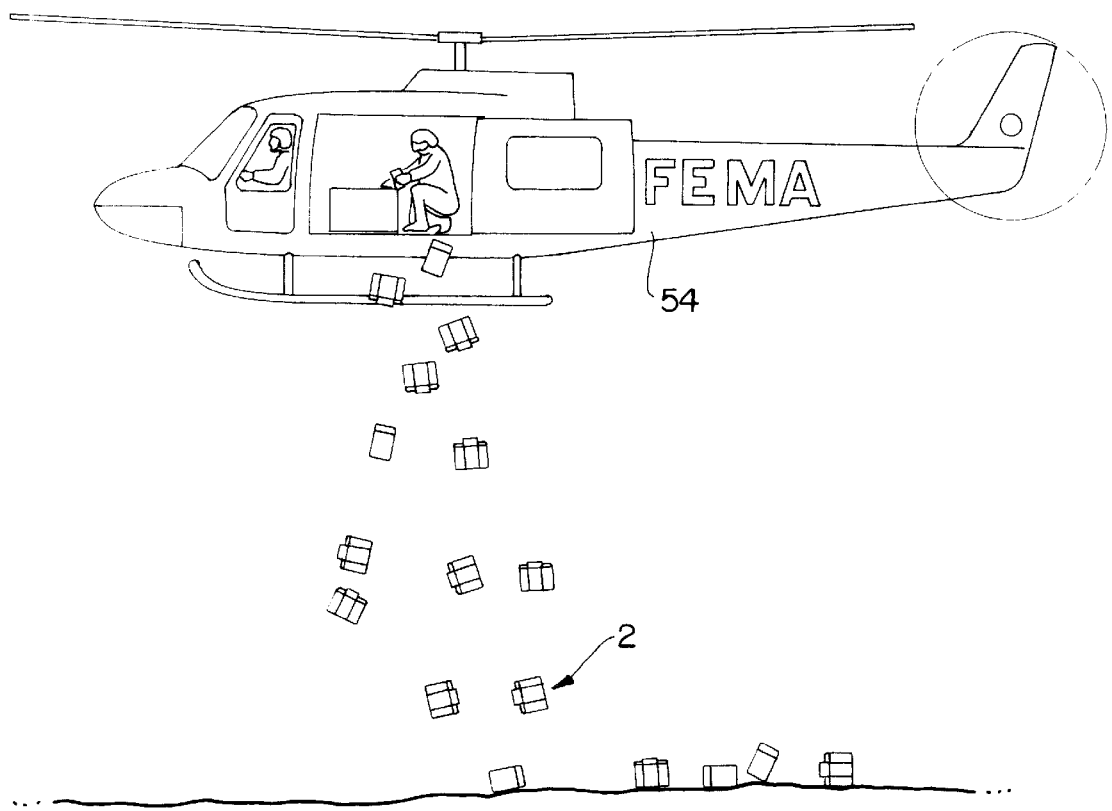
FIG. 10 shows a FEMA helicopter dropping emergency containers of the present invention into disaster areas on land or water.
Figure 11:
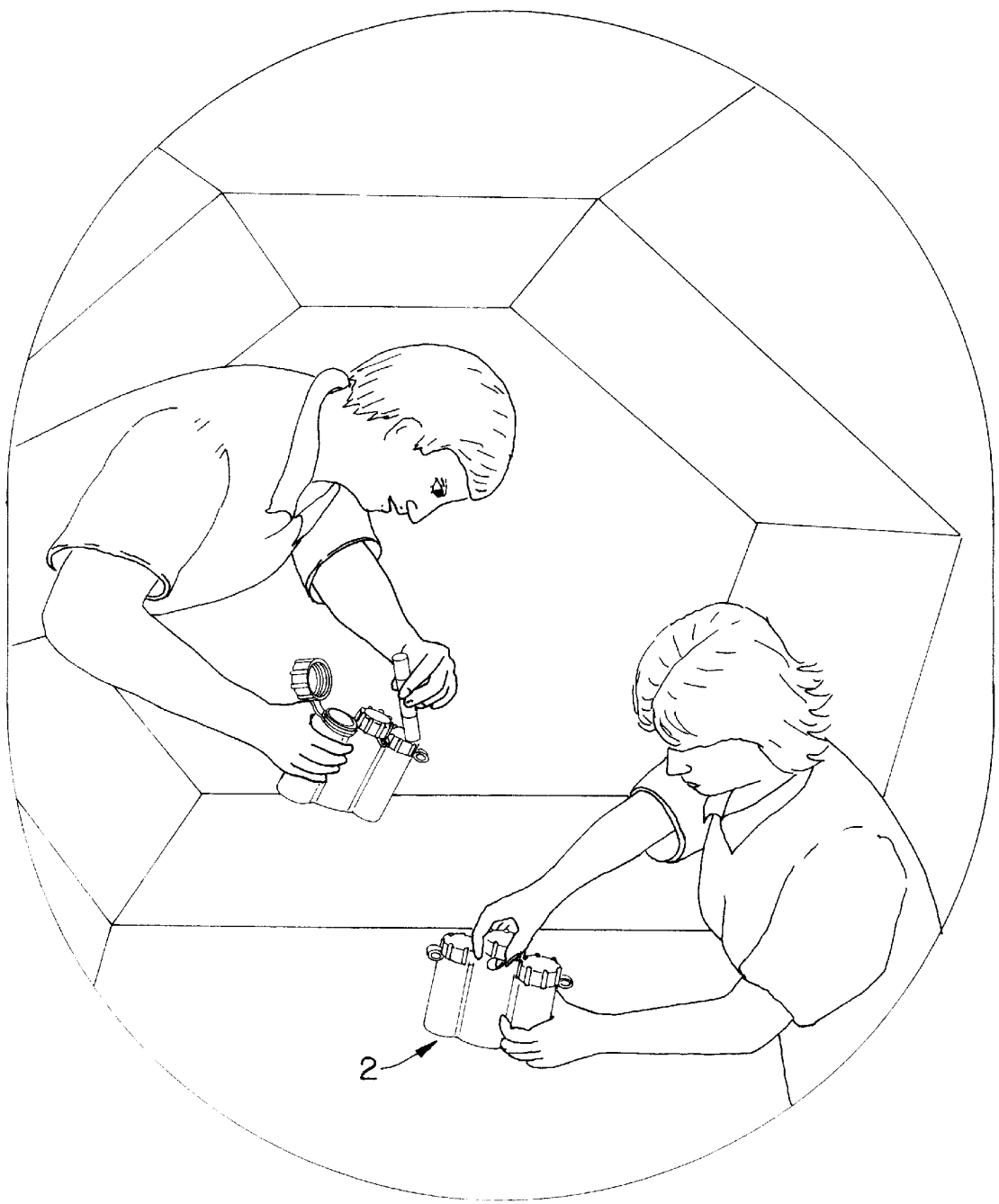
FIG. 11 shows astronauts using the containers of the present invention as an emergency back-up system.

Another primary 4 or secondary 24 container comprises an upper compartment and a removable lower compartment as shown in FIG. 9. The two compartments are held together by screwable threads, and there is an O-ring 20 between the upper and lower compartment to ensure a watertight condition. The upper compartment may be used to hold water and the lower compartment may be used to hold food.

A plurality of essentials for survival may be delivered to survivors of natural disasters with the above container 2. The central primary container 4 is filled with water. One of the secondary containers 24 is filled with healthful pills, tablets or mini-bars. Another secondary container 24 contains a first aid kit. Other secondary containers 24, if present, are reserved for supplies peculiar to the type of disaster encountered or may contain additional water. Examples of additional supplies are flashlights, miniature radios, and chemical hand warmers.

Particular contemplated uses of the containers 2 of this invention will now be discussed.

It is contemplated that some of these filled disaster survival containers 2 will be stored in FEMA distribution sites and taken by truck or helicopter 54 to areas where they are needed. If distributed by helicopter 54, the fact that the containers 2 will float and are luminous is an advantage leading to the possibility of being successfully delivered.

An additional use of the containers 2 filled with pure water, oxygen enhancers, healthful oral pills, tablets or mini-bars and miscellaneous items is aboard spacecraft or space stations for back-up emergency supplies.

The containers 2 of the present invention are also suitable for general use in carrying and storing objects which should be protected from changes in temperature and physical jarring.

While the fundamental novel features of the invention have been pointed out, it will be understood that various omissions and substitutions and changes of the form and detail may be made by those skilled in the art without departing from the spirit of the invention.

The features of the invention in which an exclusive right is claimed are defined as follows:

I claim:

1. An emergency thermally insulating container having a bottom and a top, comprising: spaced inner and outer cylindrical walls joined at the top and bottom to form a cylindrical body, a removable top cover having a centrally located indentation which contains a compass, and an O-ring between the cylindrical body and the removable top, said bottom and said top cover containing bumpers.

2. The container of claim 1, wherein the container is hypoallergenic.

3. The container of claim 1, wherein the container is luminous.

4. The container of claim 1, wherein the space between the inner and outer walls is reinforced.

5. The container of claim 1, wherein the container comprises an upper compartment and a removable lower compartment.

6. The container of claim 5, wherein the upper and lower compartments are connected by threads.

7. The container of claim 6, wherein there is an O-ring between the upper and lower compartments.

8. An emergency thermally insulating container comprising:
   A) a primary container having a top and a bottom, comprising spaced inner and outer cylindrical walls joined at the top and bottom to form a cylindrical body, and a removable top cover having a centrally located indentation which contains a compass, the container having a cylindrical inner shape and
   B) a plurality of secondary containers having bodies affixed to the outer cylindrical wall of the primary container, which secondary containers have attached removable covers.

9. The emergency container of claim 8, wherein a signaling mirror is affixed to the cover of a secondary container.

10. The emergency container of claim 8, wherein the emergency container is luminous.

11. The emergency container of claim 8, wherein the emergency container is hypoallergenic.

12. The emergency container of claim 8, wherein the space between the inner and outer walls is reinforced.

13. The emergency container of claim 8, wherein at least one secondary container contains an insertable container which can be removed from the secondary container.

14. The emergency container of claim 8, wherein there are O-rings between the covers and the bodies of the containers.

15. The emergency container of claim 8, wherein the container contains bumpers around the periphery of the top and bottom of the primary and secondary containers.

16. The emergency container of claim 8, wherein a secondary container has squeezable sides and is suitable for carrying products selected from the group consisting of food paste, ointment, and cream.

17. The emergency container of claim 8, wherein a secondary container comprises an upper compartment and a removable lower compartment.

18. The emergency container of claim 17, wherein the upper and lower compartment of the secondary container are connected by threads and there is an O-ring between the upper and lower compartments.

* * * * *